United States Patent [19]

Barker et al.

[11] Patent Number: 4,713,118

[45] Date of Patent: Dec. 15, 1987

[54] SOLUBILIZATION AND HYDROLYSIS OF CARBOHYDRATES

[75] Inventors: Sidney A. Barker; Peter J. Somers, both of Birmingham, England

[73] Assignee: Imperial Chemical Industries PLC, London, England

[21] Appl. No.: 561,148

[22] Filed: Dec. 14, 1983

Related U.S. Application Data

[63] Continuation of Ser. No. 278,614, Jun. 29, 1981, abandoned.

[30] Foreign Application Priority Data

Jul. 11, 1980 [GB] United Kingdom ................ 8022715

[51] Int. Cl.$^4$ .......................... F24C 5/20; C07H 1/00; C08B 37/00; C08B 31/00

[52] U.S. Cl. ....................................... 127/38; 127/36; 127/37; 536/1.1; 536/56; 536/102

[58] Field of Search ............................ 127/36, 37, 38; 536/1.1, 4.1, 56, 18.7, 20, 55.3, 103, 102

[56] References Cited

U.S. PATENT DOCUMENTS 4,018,620 4/1977 Penque ................................. 127/37

FOREIGN PATENT DOCUMENTS 174713 7/1936 U.S.S.R. .

OTHER PUBLICATIONS

Hunter, J. Chem. Soc., pp. 2643-2648 (1928).
Pearce et al., J. Phys. Chem., 42: 455-467 (1938).
Chem. Abs. 83: 45087p (1975).
Chem. Abs. 79: 80614x (1973).
Chem. Abs. 51: 17212 (1957), Litvak.
Chem. Abs. 33: 3586-7 (Demidchuk et al.).

*Primary Examiner*—Robert J. Warden
*Assistant Examiner*—Shawn P. Foley
*Attorney, Agent, or Firm*—Cushman, Darby & Cushman

[57] ABSTRACT

A process for the modification, solubilization and/or hydrolysis of a glycosidically linked carbohydrate having reducing groups using a mixture comprising water, an inorganic acid and a halide of lithium, magnesium or calcium. The process is particularly useful for converting cellulose (derived for example from waste-paper, wood or sawdust) or starch to glucose. When cellulose is the starting material the preferred halide is a lithium halide. When starch is the starting material a magnesium halide is preferred.

8 Claims, No Drawings

SOLUBILIZATION AND HYDROLYSIS OF CARBOHYDRATES

This is a continuation of application Ser. No. 278,614, filed June 29, 1981, now abandoned.

This invention relates to the solubilisation and hydrolysis of glycosidically linked carbohydrates having reducing groups and in particular to the solubilisation of cellulose or starch and hydrolysis of cellulose or starch to soluble oligosaccharides and/or glucose.

Cellulose is a polysaccharide which forms the principal component of the cell walls of most plants. It is a polymer of β-D-glucose units which are linked together with elimination of water to form chains of 2000-4000 units. In plants it occurs together with polysaccharides and hemicelluloses derived from other sugars such as xylose, arabinose and mannose. In the woody parts of plants cellulose is intimately mixed and sometimes covalently linked with lignin. Wood, for instance, normally contains 40-50% cellulose, 20-30% lignin and 10-30% hemicelluloses together with mineral salts, proteins and other biochemical compounds.

Degradation of cellulose may be brought about by various treatments, including treatment with acids and with enzymes present in certain bacteria, fungi and protozoa, and results primarily in the cleavage of the cellulose chain molecules and consequently in a reduction of molecular weight. Partial hydrolysis with acids produces a variety of products, often termed "hydrocelluloses", whose properties are determined by the hydrolysis conditions employed. Complete acid hydrolysis of cellulose produces glucose. Treatment with acid by solution and reprecipitation often increases the accessibility and susceptibility of cellulose to attack by enzymes, microbes and chemical reagents. Degradation of cellulose by enzymes leads to various intermediate products depending upon the enzyme employed, the final products of enzymic degradation of cellulose being generally glucose but with microbes may proceed to mainly ethanol, carbon dioxide and water.

A number of studies have been made of the effects of cellulase enzymes upon cellulose. It is recognised that cellulases degrade the more accessible amorphous regions of cellulose but are unable to attack the less accessible crystalline regions. T Sasaki et al (Biotechnol. and Bioeng., 1979, 21, 1031-1042) have shown that cellulose dissolves in 60% sulphuric acid and that when it is reprecipitated its crystalline structure has disappeared. The biological susceptibility to cellulase of the thus treated cellulose is markedly increased and it can be solubilised to an extent of about 95% and saccharified to an extent of 94% in 43 hours. The reported results with an untreated cellulose control are poor, only 26% saccharification being achieved after 48 hours.

A Girard (Ann. Chim. Phys., 1881, 24, 337-384) has shown that anhydrous hydrogen chloride gas has no effect upon cellulose, a finding confirmed recently by T P Nevell and W R Upton (Carb. Res., 1976, 49, 163-174). These latter workers however stress the important effects of the presence of small amounts of moisture.

A number of industrial processes have been developed or proposed for the production of glucose by acid hydrolysis of cellulose. These include:

1. The Bergious F Process (described in Ind. Eng. Chem., 1937, 29, 247 and in F.I.A.T. Report No. 499, Nov. 14, 1945, pages 10 and 11) in which HCl is employed and is recovered by vacuum stripping. An improved version of this process is described by J Schoenemann (Chem. Ind. (Paris), 1958, 80, 140) who claims a high glucose yield (in the order of 90% of the potential glucose) in a total reaction time of the order of 7 hours.

2. The Noguchi-Chisso Process which uses the effect of small amounts of moisture and which requires 5% HCl at a temperature of 100° C. for 3 hours, by stagewise contercurrent contact of cellulose with HCl gas at temperatures in the range −5° to 125° C. This process is described by M R Ladisch (Process Biochem., January 1979, p 21) who claims conversions of 95% on cellulose and 23% on hemicellulose.

Processes for the treatment of cellulose containing materials such as wood pulp and paper with acids or cellulose enzymes to produce simpler products such as glucose have to date had limited commercial significance for a number of reasons, their principal disadvantages being the relatively slow rate at which acids and cellulose enzymes attack cellulose and a requirement in most instances for a prior de-lignification of the cellulose containing material before treatment with acid or enzyme can be carried out successfully.

According to the present invention we provide a process for the modification, solubilisation and/or hydrolysis of a glycosidically linked carbohydrate having reducing groups to produce one or more of the effects (A) modification of the carbohydrate to induce increased accessibility and susceptibility to enzymes microbes and chemicals, (B) solubilisation of the carbohydrate, and (C) solubilisation and hydrolysis of one or more glycosidic linkages in the carbohydrate to produce soluble oligosaccharides and/or glucose wherein the carbohydrate is contacted with a mixture comprising an aqueous inorganic acid and a halide of lithium, magnesium and/or calcium or a precursor of said halide.

Products of solubilisation and/or hydrolysis include higher saccharides tri-, di-saccharides and monosaccharides. Specifically the products from cellulose include cellodextrins, cellotriose, cellobiose and glucose. When the process is used to produce carbohydrate of enhanced susceptibility, the susceptible carbohydrate may be further treated to produce solubilisation and/or degradation products. For instance the susceptible carbohydrate may be treated with an enzyme in which case the exact nature of the products will depend upon the enzyme employed and the reaction conditions. In the case of cellulose treatment with cellulase enzymes will lead under appropriate conditions to the production of glucose.

The glycosidically linked carbohydrate can be present in any suitable state. Thus it can be present as free or combined carbohydrate, in its natural state or in the form of a manufactured article. The process is particularly advantageous in its application to insoluble or otherwise immobilised carbohydrates such as cellulose alone or admixed with other constituents in e.g. wood, straw, mechanical pulp, chemical pulp, newspaper, cardboard, bagasse, corn stover, cotton, other natural sources, agricultural products, waste products, by products or manufactured products. The process is also applicable to carbohydrates which exist in highly oriented forms such as crystalline cellulose and other ordered structures which are normally highly inaccessible to enzymes and other catalysts. Such inaccessibility may be compounded by the occurrence of a polysaccharide with other polymers such as the cellulose with lignin. The process of the invention is applicable to the modification or solubilisation of cellulose without prior delignification.

The process is applicable to all glycosidically linked carbohydrates whether the glycosidic linkage is a β-linkage as in cellulose, yeast glucan or laminarin, or a α-linkage as in starch, glycogen, dextran or nigeran. Whilst those mentioned are naturally occurring polymers of D-glucose, the process is also applicable to glycosidically linked carbohydrates with other constituent pentoses, hexoses, heptoses, amino sugars or uronic acids. Such polymers having industrial significance include wood hemicelluloses, yeast mannan, bacterial and seaweed alginates, industrial gums and mucilages and chitin. Carbohydrates containing O-sulphate, N-sulphate, N-acetyl, O-acetyl and pyruvate groups can also be treated by the process of the invention as can carbohydrates derived by carboxymethylation, acylation, hydroxyethylation and other substitution processes, provided that such carbohydrates contain glycosidic linkages. Acid labile substituents on carbohydrates may be lost during the process of the invention.

Preferred acids are hydrochloric, hydrobromic and hydriodic acids, hydrochloric acid being most economical and especially preferred. The acid can be used to dissolve the lithium or magnesium halide or a precursor thereof. When sulphuric acid is used, it is preferably used in combination with a halide rather than a precursor thereof particularly a sulphate precursor.

In the mixture used in the process of the invention lithium halides are preferred for the solubilisation of cellulose, lithium chloride being especially preferred. Magnesium halides are preferred for the solubilisation and hydrolysis to D-glucose of starch, magnesium chloride being especially preferred. Other metal salts, particularly higher alkali metal halides such as sodium chloride and potassium chloride, may be present in addition to the lithium magnesium and/or calcium halides. Suitable halide precursors include carbonates, bicarbonates, and hydroxides, particularly lithium carbonate, lithium hydroxide, magnesium carbonate and magnesium hydroxide. When halogen-containing acids are used the halide of the acid is preferably the same as that of the lithium, magnesium and/or calcium halide, e.g. hydrochloric acid is used, for preference, with lithium chloride. The treatment may take place in two stages, e.g. in the treatment of cellulose a lithium halide followed by a magnesium halide may be used.

The concentration of the acid used may vary within a wide range up to 10 molar. When the process is used to render the carbohydrate more accessible and susceptible to enzymes, microbes and chemicals with limited or selective carbohydrate solubilisation the preferred concentration is 1 molar or less. When complete solubilisation of the carbohydrate is desired, the preferred concentration is up to 4 molar, particularly 1–4 molar, but can be higher, i.e. up to 10 molar, in certain cases for example when treating polysaccharides such as chiten.

Preferred lithium, magnesium and/or calcium halides are the chlorides, bromides and iodides, chlorides being most economical are especially preferred. Preferably the concentration of these halides in the acid is >1M, saturated solutions being particularly suitable. Effective concentrations of >8M of lithium halides in appropriate acids can be achieved at ambient temperature or at temperatures suitable for the limited objective of increasing the accessibility and susceptibility of the carbohydrate to subsequent enzyme attack. In general the higher the concentration of a halogen acid employed in the process the lower the concentration of the lithium, magnesium or calcium halide in saturation at room temperature. The salts lithium chloride, lithium bromide and lithium iodide all have good solubility in aqueous solutions of their corresponding halogen halides at room temperature. This is not the case however with lithium fluoride in hydrofluoric acid. Lithium halides can also be used together with other acids, such as sulphuric acid, in which they dissolve (although total solubility of lithium salt in sulphuric acid is limited), or trifluoroacetic acid in which two layers form. However lithium halides in halogen acids are preferred. Magnesium halides have more limited solubility than lithium halides in halogen acids. A saturated solution (12.65M) of lithium chloride in 1.05M hydrochloric acid at 25°, contains 54.64 g LiCl. A saturated solution (11.3M) of lithium chloride in 4M hydrochloric acid at 20° C. contains an estimated 47.9 g LiCl.

The temperature of contacting the carbohydrate with the mixture may be varied within a wide range from −5° C. to 125° C. If the objective is to render the carbohydrate more accessible and susceptible to enzymes, microbes or chemicals with limited or selective solubilisation of carbohydrate then the temperature is preferably in the range from 0°–50° C., particularly between 4°–22° C. When complete solubilisation of the carbohydrate is required the temperature range is suitably from 4°–100° C. with a preference between 50°–90° C. For hydrolysis of the glycosidic linkages in the carbohydrate although the rate is appreciable at ambient temperatures the preferred range is 50°–100° C., particularly 50°–90° C.

The particularly advantageous part of the process is the short duration of the carbohydrate contacting process with the mixture to achieve modifying effects much greater than those produced by any one or two of the components of the contacting mixture alone. From experience it is evident that the pretreatment to improve accessibility and susceptibility to enzymes, microbes and chemicals can be shortened to 1–24 hours at room temperature or below. Complete solubilisation of the carbohydrate is generally achieved within one hour at 50° C. but is a few minutes only at 90°–100° C. particularly if the concentration of the undissolved carbohydrate is low, the amount remaining undissolved is low or the carbohydrate has been previously contacted at 50° C. or below. While a carbohydrate, particularly one originally insoluble in the modifying mixture, may be already nearly 50% hydrolysed at the time solubilisation is achieved, it appears advantageous to await such solubilisation at 50° C. or below before heating for the few further minutes required at 90°–100° C. to complete the hydrolysis to its highest extent without undue degradation.

During the hydrolysis stage, some of the water in the contacting mixture is consumed and this becomes important in the presence of high concentrations of soluble carbohydrate. Thus 162 g of cellulose when completely hydrolysed to glucose will have consumed 18 g of water. Since this will both increase the concentration of the acid employed and denude the lithium/magnesium/calcium halide of water, appropriate steps are preferably taken to remedy this at high carbohydrate concentrations.

In practice the amount of carbohydrate suspended originally in the mixture varies according to the nature of the carbohydrate, the physical state in which it occurs, its accessibility in that state, and the degree of polymerisation of the carbohydrate. With cellulose, where suspension presents some difficulties, 5-10% concentrations are easily achievable and 15% concentration with care. In general the limiting factor becomes mainly one of viscosity bringing attendant problems of heat transfer and effective mixing. If hydrolysis is allowed to proceed then further amounts of the carbohydrate can be solubilised. The addition of water consumed in the hydrolysis also becomes important in this respect as does the effective concentration of the acid. Starch, even in the intact starch grain, can be solubilised by a mild treatment with the contacting mixture often below its gel point. This is illustrated with the solubilisation and hydrolysis of starch (Amylum maydis) with hydrochloric acid (2.0M) saturated with $MgCl_2$ where treatment at 50° for 3 hours followed by 90° for 12 minutes gives most effective conversion to D-glucose. This combines the effect of the added $MgCl_2$ in facilitating the solubilisation of starch at low temperatures with an accelerated rate of hydrolysis to D-glucose at a higher termperature.

Carbohydrates present in micro-organisms, mammalian tissues, plant tissues, and other natural sources can be effectively extracted even if chemically attached therein to proteins or lipids. Pretreatment of such tissues or even the isolated carbohydrates, under milder conditions that avoid excessive solubilisation enables enzymes and microbes to attack their substrates in a subsequent stage faster and more effectively than untreated tissues, carbohydrates or carbohydrate containing materials.

Major savings in the amount of enzyme or other catalyst can be achieved amounting to a factor of at least ten over a typical process having no such pretreatment steps. The contacting mixture employed is available for recycling for reuse.

A LiCl-HCl-$H_2O$ mixture differed from NaCl/HCl/-$H_2O$ in its behavior on a Biogel P2 column. The LiCl-HCl is excluded from the packing matrix when the mixture is injected whereas sodium chloride is included.

Most importantly the process of the invention is used in the production of glucose from cellulose or starch. Other products which can be produced include glucose, yeast glucan, glucosamine from chitin, hexuronic acids from polyuronides, xylose from xylan and hemicellulose, sugars from their glycosides and the disruption, solbilisation and hydrolysis of carbohydrates in the cell walls of tissues and microbes. Alternatively the process may be used to produce a modified polysaccharide or cellulose which can be used in that form to spin fibres, non-woven fabrics or other articles such as films or membranes by continuous injection into a liquid immiscible with the reaction mixture but from which the modified polysaccharide or cellulose is precipitated.

The process of the invention has a number of advantages as applied to cellulose viz:

1. A prior delignification step is not required.

2. Pretreatment may be chosen to minimise solubility whilst retaining subsequent accessibility to enzyme action.

3. Pretreatment renders all the cellulose accessible to subsequent enzyme action, rather than merely a fraction thereof.

4. The pretreatment can be applied to a variety of polymers alone or as mixtures e.g. cellulose and hemicellulose to provide ready accessibility to subsequent hydrolysis.

5. Enhanced rate of attack by cellulase and hence lower enzyme requirement for complete reaction.

6. A versatile, aqueous based, solubilising agent giving control over solubilisation and hydrolysis.

7. A mode of action that is rapid in both the heterogeneous and homogeneous phases.

8. Acceleration of the rate of hydrolysis with respect to an aqueous acid of the same solution molarity enabling a given rate of hydrolysis to be achieved at a lower temperature than with an aqueous acid of the same solution molarity.

9. The ability to deal with high concentrations of cellulose in particularly the heterogeneous phase due to the measure of control that can be exerted.

In the application of the process to other members of the wide range of naturally occurring and synthetic carbohydrates containing one or more glycosidic linkages and having a spectrum of solubilities and susceptibility to the reagents of the process, optimisation of conditions along the lines given more particularly for cellulose are within the competence of workers skilled in the art. In the detailed designing of particular processes for particular polysaccharides based on the reagents of the invention two features can be clearly delineated. The first is the original accessibility and susceptibility to the reagents of the invention of the polysaccharide in the material in which it occurs which will differ for the same polysaccharide in different environments, and different physical forms. The second feature is the accessibility and susceptibility of the glycosidic linkages in the particular polysaccharide to the reagents of the invention once the carbohydrate is solubilised.

Here the process offers further advantages applied to both cellulose and other carbohydrates containing glycosidic linkages since the reagents of the invention can be further manipulated during the process to attain the desired objectives of that process. The following are a list of parameters that are not exclusive within the terms of the invention but indicate the factors over and above those already mentioned that fall within the claims of the invention and which would be applied by those skilled in the art.

1. Addition of water over and above that consumed by the hydrolysis of the glycosidic linkages in the carbohydrates. Such water may be added at any stage of the process but preferably once solubisation of the carbohydrate has been achieved. It is intended that steam is included among the forms in which water is added.

2. Addition of an alkali, carbonate or bicarbonate once carbohydrate solubilisation has been achieved to decrease the overall acid concentration of the reaction mixture used in the process.

3. Removal of hydrogen halide from the reagents of the reaction mixture during the course of the process by application of reduced pressure.

4. The reduction of the metal halide concentration during the course of the process by addition of aqueous acid.

5. Simultaneous addition of both further carbohydrate and water during the course of the process.

6. Use of some or all of the acid component of the reagents in the form largely insoluble in or immiscible with the rest of the reagents.

7. The use of a closed system in which the carbohydrate is contacted with the mixture at a pressure that may be above or below that of atmospheric pressure.

8. The removal of a product of the reaction during the course of the reaction either continuously or discontinuously.

9. The introduction of a second phase immiscible with the first that can be either gas, liquid or solid that performs one or more functions of agitation of the reaction mixture, specific or selective partitian of a product or reactant, heat transfer, or modifies the reaction to prevent undue production of unwanted by-products.

The invention is illustrated by the Examples given below. In these Examples the analytical methods and the compositions of the materials used were as follows:

(a) Determination of total carbohydrate

The cysteine-sulphuric acid reagent (700 mg of L-cysteine hydrochloride monohydrate in 1 liter 86% sulphuric acid) was added to a portion of the sample/-standard such that the ratio of reagent to sample/standard was 5:1 (normally 5 $cm^3$:1 $cm^3$). The reagent was added to sample in tubes immersed in an ice bath. The tubes were than placed in a boiling water bath for 3 minutes, after which time they were removed and allowed to cool to room temperature. The absorbance of each solution was measured at 420 nm and the carbohydrate concentration obtained, by reference to appropriate standards, to give the results quoted in the Examples.

(b) Determination of reducing sugars

Buffer: Sodium acetate-acetic acid; 0.05M, pH 4.8.

Reagent: Potassium ferricyanide (0.117 g) and Sodium carbonate (1.95 g) were dissolved in distilled water and diluted to 100 $cm^3$. This solution was freshly prepared each morning.

Standard solutions (0–600 $\mu g\ cm^{-3}$ of D-glucose; 0.4 $cm^3$) or sample solutions (0.4 $cm^3$) were added to test-tubes, cooled in an ice bath, containing reagent (2.0 $cm^3$) and buffer (1.5 $cm^3$). After mixing, the test-tubes were held in a boiling water bath for 5 minutes, and thereafter cooled to room temperature. The reaction mixtures were diluted by addition of water (4.0 $cm^3$) and the absorbance of each solution measured at 420 nm. The difference in absorbance between standard or sample and a blank (prepared by replacement of sample with water) enabled calculation of reducing sugar content expressed with respect to D-glucose.

(c) Determination of D-glucose

Buffer: 2-Amino-2-(hydroxymethyl)-propane-1,2-diol (TRIS), 0.5M, pH 7.0

Reagent A: Glucose Oxidase (19,500 units per g., 50 mg.) dissolved in buffer (50 $cm^3$)

Reagent B: Peroxidase (ex horse radish, 90 units per mg., 10 mg.) and 2,2'-Azino-di-(3-ethyl benzthiazoline sulphonic acid (ABTS, 50 mg.) dissolved in buffer (100 $cm^3$).

Standard solutions of D-glucose or unknown solutions containing D-glucose (0 to 0.1 mg per $cm^3$, 0.2 $cm^3$) were mixed with reagent A (0.5 $cm^3$) and reagent B (1.0 $cm^3$). After 30 minutes at 37° C., the absorbance of each solution was measured at 420 nm. and the D-glucose concentration of the unknown solutions determined by reference to the calibration with D-glucose standard solutions.

(d) Gel Permeation chromatography

Chromatography was performed on Biogel P-2 (Biclad Laboratories Limited). Two sizes of column were employed dependent on the analytical technique used for determination of material in the column eluate.

Method A:

Chromatography was performed on Biogel P-2 in a glass column (425 $cm^3$ volume, 150 cm in length) with a water jacket maintained at 60° C. The column was pumped at 0.8 $cm^3\ min^{-1}$. The column eluate was split and analysed by (i) differential refractometry (Waters Associates Model R401) operating at 0.32 $cm^3\ min^{-1}$ and/or (ii) an automated cysteine-sulphuric acid method for total hexose determination (S A Barker, M J How, P V Peplow and P J Somers, Anal. Biochem., 26, (1968), 219) operating at 0.1 $cm^3\ min^{-1}$ sample flow rate. The volume of sample applied to the Biogel P-2 column was 0 to 0.1 $cm^3$ containing 0 to 5 mg of carbohydrate.

Method B:

Chromatography was performed as in Method A except that a column (145 cm×0.6 cm internal diameter) was employed operating at a flow rate of 0.15 $cm^3\ min^{-1}$. Analysis of the column eluate was by the cysteine-sulphuric acid method for total hexose determination as in method A. The sample volume employed was 0 to 0.01 $cm^3$ containing 0 to 0.5 mg of carbohydrate.

The area under each peak of carbohydrate material was integrated and compared with the area produced by a standard of D-glucose. The results were expressed as a percentage of the total carbohydrate determined in the eluate. Where the products were an oligomeric series the nomenclature G1, G2 - - - Gn is used to indicate the number of sugar units in each oligomer.

(e) Moisture contents

Analytical results presented are based on the weights taken for analysis and do not allow for moisture unless stated otherwise.

Moisture contents observed, on drying at 55° in vacuo over $P_2O_5$, were:

Cellulose fibres, Whatman Chromedia CF11: 3.7%

Mechanical pulp: 8.1%

Newsprint: 7.2%

(f) Composition of materials (i) Cellulose content

Duplicate samples (ca 25 mg) were accurately weighed into stoppered test-tubes and sulphuric acid (98%, 1 $cm^3$ MAR grade) added. The temperature of these suspensions was maintained below 0° C. by means of an ice/salt bath (−10° C.) After 48 hours at 4° distilled water (8.0 $cm^3$) was added and the tubes heated for 2½ hours in a boiling water bath. After cooling to room temperature the D-glucose and total carbohydrate contents were determined.

The results obtained by this procedure are set out in Table 1a.

TABLE 1a

Composition of materials used expressed as weight percentage with respect to cellulose on a dry weight basis.

| Sample | D-glucose content | Total carbohydrate content |
|---|---|---|
| Cellulose fibres | | |
| 1 | 96.5 | 97.5 |
| 2 | 97.8 | 88.0 |
| Mechanical pulp | | |
| 1 | 41.0 | 41.0 |
| 2 | 41.0 | 41.0 |
| Newsprint | | |
| 1 | 56.0 | 55.0 |
| 2 | 63.0 | 66.0 |

(ii) Content of easily hydrolysable neutral carbohydrates arising from non-cellulose polysaccharides (e.g. hemicellulose).

Samples (50–60 mg) of dried material were weighed accurately into test-tubes and trifluoroacetic acid (2.0M, 2.0 $cm^3$) added. The tubes were sealed and heated in a boiling water bath for 6 hours. After cooling, and opening of the tubes, trifluoro acetic acid was removed by evaporation. The residue was taken up in borate buffer (0.13M, pH 7.5, 1.0 $cm^3$) and analysed using borate anion exchange chromatography (JEOL carbohydrate analysis system). The results obtained by this procedure are set out in Table 1b.

TABLE 1b

Content of neutral sugars in trifluorocetic acid hydrolysates arising from non-cellulose polysaccharides expressed as a weight percentage of dry weight

| Component (or time of elution if unidentified) | Cellulose fibres | Mechanical pulp | Newsprint |
|---|---|---|---|
| 30 min | 0.03 | 0.9 | 0.45 |
| 35 min | 0.05 | — | — |
| rhamnose | — | 0.13 | 0.10 |
| 92 min | — | 0.12 | 0.15 |
| 144 min | — | 0.24 | 0.17 |
| mannose | trace | 7.27 | 3.90 |
| arabinose (or fructose) | — | 0.92 | 0.54 |
| galactose | trace | 1.60 | 0.86 |
| xylose | 0.14 | 2.73 | 1.89 |
| Total non-glucose neutral carbohydrates | 0.22 | 13.91 | 8.06 |
| glucose | 3.32 | 3.49 | 2.26 |
| celloboise | 0.03 | 0.11 | 0.10 |

EXAMPLE 1

Pretreatment of cellulose with solutions containing lithium halides, followed by digestion with cellulase Preliminary work established that pretreatment of cellulose fibres with saturated solutions of lithium chloride or lithium iodide for 24 hours gave a significant increase in the initial rate of hydrolysis of the water washed, pretreated, cellulose by cellulase over periods of 60 minutes at 50° C.

Samples (100 mg) of cellulose fibres were treated with solutions containing lithium chloride or lithium iodide respectively for 24 hours at room temperature. The fibres were allowed to settle and the supernatant liquor removed by decantation. The fibres were washed with distilled water (2×10 $cm^3$) and resuspended in acetate buffer (0.05M, pH 4.8). Cellulase (Maxazyme-CL2000, GIST, 1% w/v in acetate buffer, 0.05M, pH 4.8, 4.0 $cm^3$) was added. The digestion was carried out at 50° C. and aliquots (0.4 $cm^3$) removed at 10 minute intervals. The content of reducing sugar was determined. The results obtained are set out in Table 2.

TABLE 2

Rate of digestion of cellulose by cellulase after pretreatment with solutions of lithium halides

| Pretreatment | $H_2O$ | LiI (Sat) | LiCl (Sat) |
|---|---|---|---|
| Rate of production of reducing sugar (with respect to glucose) $\mu g\ cm^{-3}\ min^{-1}$ | 7.6 | 10.4 | 10.4 |

EXAMPLE 2

Pretreatment of cellulose with saturated solutions of lithium chloride and lithium iodide, followed by digestion with cellulase Samples (100 mg) of cellulose fibres were pretreated with saturated aqueous solutions of lithium chloride or lithium iodide, and distilled water as a control, for 24 hours at room temperature. The fibres were allowed to settle and the supernatant liquid removed by decantation. The fibres were washed with distilled water (2×10 $cm^3$) and suspended in buffer (10 $cm^3$). After stirring at 50° C. for 10 minutes, cellulase solution (1% w/v in buffer as in Example 1, 5.0 $cm^3$) was added and digestion allowed to proceed at 50° C. Samples (0.5 $cm^3$) were removed after 1, 2, 4, 6, 24, 48, 96 and 100 hours, immediately diluted to 5.0 $cm^3$ and stored at 4° C. When all samples had been collected analysis for reducing sugars were performed, using dilution where appropriate for high concentrations of reducing sugars, and for total carbohydrate. The molecular distribution was examined by gel fermentation chromatography. The results obtained are set out in Table 3. It can be seen from this data that the pretreatment with saturated lithium chloride solutions provides a greater rate of production of reducing sugar by cellulase and 95% conversion to available glucose after 24 hours. Saturated lithium iodide pretreatment afforded an increased rate of solubilisation and hydrolysis over that observed with water pretreatment (after 24 hours 77% conversion as compared to 70% with water) but was not as effective as the pretreatment with saturated lithium chloride solution. Total carbohydrate analysis and gel permeation chromatography confirm the reducing sugar analysis and indicate the predominant product to be glucose with small amounts of cellobiose and other oligomers. All three materials reached essentially complete hydrolysis after 100 hours.

TABLE 3

Analysis of samples from cellulase treatment of cellulose pretreated with saturated aqueous solutions of lithium chloride, lithium iodide or water.

| Time of Cellulase action | Pretreatment: Distilled water | Saturated lithium iodide solution | Saturated lithium chloride solution |
|---|---|---|---|
| | % conversion as expressed by reducing sugar analysis | | |
| 1 | 10 | 11 | 12 |
| 2 | 24 | 26 | 33 |
| 4 | 31 | 34 | 39 |
| 6 | 56 | 57 | 57 |
| 24 | 70 | 77 | 95 |
| 48 | 91 | 94 | 97 |
| 96 | 98 | 97 | 96 |
| 100 | 97 | 97 | 99 |
| | % conversion as expressed by total sugar analysis | | |
| 100 | 98 | 97 | 100 |
| | Relative proportion of oligomers by gel permeation chromatography | | |
| 100 G1 | 98.0% | 96.0% | 98.7% |
| G2 | 2.0% | 1.0% | 0.8% |
| G > 2 | 0 | 3.0% | 0.5% |

EXAMPLE 3

Effect of lithium chloride and sodium azide on digestion of cellulose by cellulase (i) sodium azide Materials which inhibit microbial growth are usually added to enzyme solutions to prevent microbial growth and inhibit production of unwanted material. The effect of sodium azide on the rate of production of reducing sugar from cellulose using cellulase was determined. Duplicate samples of cellulose fibres (100 mg) were pretreated, for 73 hours, with distilled water at room temperature. After the fibres had settled the supernatant liquid was removed by decantation and buffer (10 $cm^3$) added. Following the procedure of Example 2 the suspensions were digested with cellulase or cellulase containing sodium azide (150 mg). The results of the analysis are set out in Table 4. The digestion in the presence of sodium azide gives little difference in rate of production of reducing sugar compared with the corresponding control without sodium azide. With sodium azide there is a higher proportion of cellobiose in the final solution than is the case with the control. This may be due to inhibition of a cellobiase by sodium azide.

TABLE 4

Effect of sodium azide on the digestion of cellulose by cellulase

| Time of digestion | % conversion as expressed by reducing sugar analysis: Cellulase | Cellulase and sodium azide |
|---|---|---|
| 1 | 12 | 14 |
| 2 | 17 | 20 |
| 4 | 32 | 28 |
| 6 | 35 | 36 |
| 24 | 78 | 70 |
| | Relative proportion of oligomers by gel permeation chromatography | |
| 24 G1 | 95% | 80% |
| G2 | 5% | 20% |

(ii) lithium chloride

In previous examples the cellulose fibres were washed with distilled water to remove residual pretreatment solution. The effect of residual lithium chloride on the rate of production of reducing sugar and final product composition was determined. A sample (100 mg) of cellulose fibres was pretreated with a solution of lithium chloride (saturated). The fibres were allowed to settle and the supernatant liquid removed by decantation. The fibres were not washed, buffer (10 $cm^3$) was added and the digestion with cellulase and analysis for reducing sugars were performed as in Example 2. A control of cellulose pretreated with distilled water was employed. The results are given in Table 5. Analysis by gel permeation chromatography show G1 and G2 in the proportion 95%: 5% respectively.

If the results obtained using unwashed, lithium chloride pretreated, cellulose fibres are compared with those using a washing stage (Example 2, Table 3) it can be seen that the initial rate for the unwashed sample exceeds that for the washed sample, but that the concentration of reducing sugar after 24 hours is higher for the washed sample. This may result from the washing procedure removing the lithium chloride from between the fibres and hence removing the swelling effect, i.e. where the swelling effect is maintained, the initial rate of attack may be enhanced. Thus removal of the pretreatment solution without washing allowed 73% hydrolysis after 6 hours compared with 57% after 6 hours with a washing step after pretreatment.

TABLE 5

Effect of residual lithium chloride on the digestion of cellulose by cellulase.

| Time of cellulase action | Pretreatment: Distilled water | Lithium chloride (saturated) |
|---|---|---|
| | % Conversion as expressed by reducing sugar analysis | |
| 1 | 12 | 42 |
| 2 | 17 | 56 |
| 4 | 32 | 71 |
| 6 | 35 | 73 |
| 24 | 78 | 85 |

EXAMPLE 4

Effect of pretreatment with saturated lithium chloride at elevated temperatures Samples of cellulose fibres (100 mg) were placed in reaction vessels and solutions of lithium chloride (saturated, 10 $cm^3$) added. The vessels were heated at either 50° or 100° C. for 1 hour. Control experiments were performed using distilled water. After the one hour pretreatment the fibres were washed with distilled water ($2\times10$ $cm^3$) and digested with cellulase for 24 hours as in Example 2. The results are set out in Table 6. The results show that no effective improvement is achieved by the use of saturated lithium chloride at 50° or 100° C. compared with pretreatment with water at the same temperatures.

TABLE 6

Effect of pretreatment with saturated lithium chloride at 50° C. or 100° C. on the subsequent digestion of cellulose by cellulase

| Time of Cellulase action | Pretreatment: Distilled water 50° C. | Distilled water 100° C. | Saturated lithium chloride 50° C. | Saturated lithium chloride 100° C. |
|---|---|---|---|---|
| | Conversion as expressed by reducing sugar analysis | | | |
| 1 | 17 | 4 | 13 | 11 |
| 2 | 21 | 14 | 21 | 17 |
| 4 | 29 | 19 | 32 | 21 |
| 6 | 36 | 28 | 34 | 30 |
| 24 | 74 | 63 | 67 | 58 |

EXAMPLE 5

Effect of saturated lithium chloride pretreatment on the digestion of other cellulosic substrates by cellulase Samples (100 mg) of mechanical pulp and newsprint (chopped in a blender) were pretreated with a saturated solution of lithium chloride (10 $cm^3$) for three weeks at room temperature. Control, pretreated with distilled water, was also prepared. The supernatant liquids were removed, with addition of distilled water (5 $cm^3$) to aid settling of the fibres, and the fibres washed with distilled water ($2\times10$ $cm^3$). Buffer solution (10 $cm^3$) was added and digestion with cellulase carried out as in Example 2. The results are set out in Table 7. The results show that prolonged treatment with saturated lithium chloride, of mechanical pulp or newsprint, achieved no improvement over water alone under these conditions.

TABLE 7

Effect of pretreatment with lithium chloride solution on the digestion of mechanical pulp and newsprint with cellulase

| Time of cellulase action | Mechanical pulp Pretreatment with: Water | Mechanical pulp Pretreatment with: Lithium chloride | Newsprint Pretreatment with: Water | Newsprint Pretreatment with: Lithium chloride |
|---|---|---|---|---|
| | % Conversion as expressed by reducing sugar analysis | | | |
| 1 | 14 | 14 | 20 | 22 |
| 2 | 15 | 15 | 25 | 24 |

TABLE 7-continued

Effect of pretreatment with lithium chloride solution on the digestion of mechanical pulp and newsprint with cellulase

| Time of cellulase action | Mechanical pulp Pretreatment with: Water | | Newsprint Pretreatment with: Water | |
|---|---|---|---|---|
| | Water | Lithium chloride | Water | Lithium chloride |
| | % Conversion as expressed by reducing sugar analysis | | | |
| 4 | 16 | 18 | 26 | 27 |
| 6 | 17 | 18 | 30 | 30 |
| 24 | 24 | 25 | 34 | 36 |

EXAMPLE 6

The effect of a solution of hydrochloric acid (1.0M) saturated with lithium chloride used as a pretreatment for cellulose containing materials prior to cellulase digestion Samples (10 mg) of cellulose fibres, mechanical pulp and newsprint were pretreated with a solution (10 $cm^3$) of hydrochloric acid (1.0M) saturated with lithium chloride at room temperature for 24 hours. After pretreatment the fibres were allowed to settle out (i) An aliquot (5 $cm^3$) of the supernatant liquid was removed and subjected to centrifugation to ensure clarification. Aliquots (0.1 $cm^3$) were removed and diluted to 10 $cm^3$. Standard solutions of D-glucose were likewise prepared and analysed for total carbohydrate and for D-glucose. The results are set out in Table 8.

(ii) The residual fibres were washed with distilled water ($2\times10$ $cm^3$) and resuspended in buffer (10 $cm^3$). Cellulase digestion was performed as in Example 2. Analysis for reducing sugar, total carbohydrate and D-glucose were performed at the five intervals tabulated, and analysis by gel permeation chromatography was conducted at the termination of cellulase digestion. The results are set out in Tables 8 and 9.

As can be seen from the data in Tables 8 and 9, pretreatment gives rise to significant solubilisation, but with limited hydrolysis, and greatly facilitates attack by cellulase on the residual cellulose.

TABLE 8

Analysis of material solubilised after pretreatment of cellulosic materials with hydrochloric acid (1.0 M) saturated with lithium chloride and after subsequent cellulase action.

| Material | Cellulose fibres | Mechanical pulp | Newsprint |
|---|---|---|---|
| % solubilised during pretreatment | | | |
| total carbohydrate | 18.8 | 16.7 | 15.7 |
| D-glucose | 5.5 | 2.5 | 1.4 |
| % solubilised after pretreatment and cellulase action | | | |
| Reducing sugar | 88.0 | 33.0 | 47.0 |
| Total carbohydrate | 92.0 | 34.0 | 43.0 |
| D-glucose | 93.0 | 19.0 | 44.0 |
| Relative molecular distribution after cellulase action (%) | | | |
| G1 | 97.5 | 44.0 | 99.0 |
| G2 | 2.5 | 52.0 | 0.5 |
| G > 2 | 0 | 4.0 | 0.5 |

TABLE 9

Effect of pretreatment with hydrochloric acid (1.0 M) saturated with lithium chloride on subsequent digestion of residual cellulosic materials by cellulase.

| Time of cellulase action | Analysis | Cellulose fibres pretreated with Water | Cellulose fibres pretreated with HCl/LiCl | Mechanical pulp pretreated with Water | Mechanical pulp pretreated with HCl/LiCl | Newsprint pretreated with Water | Newsprint pretreated with HCl/LiCl |
|---|---|---|---|---|---|---|---|
| 1 | Reducing sugar | 14 | 66 | 6 | 17 | 14 | 32 |
| | Total carbohydrate | — | 67 | — | 18 | — | 34 |
| | D-glucose | — | 68 | — | 15 | — | 31 |
| 2 | Reducing sugar | 19 | 70 | 4 | 20 | 22 | 38 |
| 4 | Reducing sugar | 30 | 64 | 10 | 25 | 26 | 36 |
| 6 | Reducing sugar | 44 | 67 | 9 | 25 | 26 | 39 |
| 24 | Reducing sugar | 70 | 75 | 15 | 28 | 33 | 41 |
| | Total carbohydrate | — | 78 | — | 29 | — | 37 |
| | D-glucose | — | 79 | — | 16 | — | 38 |

Results are expressed as % conversion

EXAMPLE 7

Detailed comparison of pretreatment of cellulose with combinations of water, hydrochloric acid and lithium chloride, and subsequent digestion with cellulase Samples (100 mg) of cellulose fibres were pretreated for 24 hours at room temperature with aliquots (10 $cm^3$) of distilled water, hydrochloric acid (1.0M) saturated with lithium chloride, distilled water saturated with lithium chloride, or hydrochloric acid (1.0M). The supernatants were analysed for solubilised carbohydrate, and the residual fibres for susceptability to cellulase digestion, as described in Example 6. The results are set out in Table 10.

From the data in Table 10 it can be seen that:

(i) Hydrochloric acid (1.0M) alone does not improve the rate of cellulase action or increase the yield of soluble carbohydrate when compared with a water pretreatment.

(ii) Both lithium chloride (saturated) and hydrochloric acid (1.0M) saturated with lithium chloride improve the rate of cellulase action and the overall yield of soluble carbohydrate and D-glucose.

(iii) Only hydrochloric acid (1.0M) saturated with lithium chloride results in appreciable solubilisation of available carbohydrate in the pretreatment.

(iv) After cellulase action for 1 hour, the cellulose fibres pretreated with hydrochloric acid (1.0M) saturated with lithium chloride, provides 95% of the available carbohydrate in solution. In the same time scale lithium chloride pretreatment permits only 64% and water pretreatment only 21% of the available carbohydrate to be solubilised.

TABLE 10

Analysis of material solubilised during pretreatment of cellulose fibres with various solutions and during subsequent digestion with cellulase
Values are corrected for moisture content of original cellulose fibres.

| Pretreatment solution | Analysis method | % Solubilised | % solubilised during action of cellulase for 1 hr | 2 hr | 4 hr | 6 hr | Total % solubilised |
|---|---|---|---|---|---|---|---|
| Distilled water 24 hours | Reducing sugar | n.d. | 15 | 17 | 24 | 41 | 41 |
| | Total carbohydrate | n.d. | 21 | 26 | 35 | 47 | 47 |
| | D-glucose | n.d. | 17 | 17 | 25 | 31 | 31 |
| HCl(1.0 M) saturated with LiCl 24 hours | Reducing sugar | 13 | 70 | 73 | 74 | 74 | 87 |
| | Total carbohydrate | 15 | 80 | 81 | 82 | 82 | 97 |
| | D-glucose | 11 | 50 | 53 | 60 | 60 | 71 |
| LiCl saturated 24 hours | Reducing sugar | n.d. | 66 | 74 | 78 | 82 | 82 |
| | Total carbohydrate | <0.1 | 64 | 70 | 79 | 82 | 82 |
| | D-glucose | n.d. | 46 | 55 | 57 | 64 | 64 |
| HCl(1.0 M) 24 hours | Reducing sugar | n.d. | 15 | 22 | 29 | 33 | 33 |
| | Total carbohydrate | n.d. | 12 | 19 | 27 | 33 | 33 |
| | D-glucose | n.d. | 17 | 19 | 24 | 31 | 31 |

n.d. = not detectable

In view of the enhanced rate of cellulose action observable after pretreatment with hydrochloric acid (1.0M) saturated with lithium chloride a further comparison was made using reduced pretreatment times and reduced cellulase levels.

Samples (100 mg) of cellulose fibres were pretreated with either distilled water (10 $cm^3$) or hydrochloric acid (1.0M) saturated with lithium chloride (10 $cm^3$) for various times at room temperature as specified in Table 11. The residual fibres were analysed for cellulase susceptability as in Example 6, using solutions of cellulase at either 1.0% or 0.1% w/v concentration. The results obtained are set out in Table 11. The results further demonstrate the enhanced effectiveness of cellulase on residual fibres after pretreatment with hydrochloric acid (1.0M) saturated with lithium chloride as compared with pretreatment with water. This enhanced effectiveness is obtainable after pretreatment times of one hour.

TABLE 11

Analysis of material solubilized during pretreatment of cellulose with various solutions and during subsequents digestion with cellulase.

| Pretreatment solution | Pretreatment time (hours) | Analysis method | % Solubilised in pretreatment | Cellulase concentration % | % solubilised during cellulase action for: 1 hr | 2 hr | 4 hr | 6 hr | 24 hr | Total % solubilised after 24 hrs |
|---|---|---|---|---|---|---|---|---|---|---|
| $H_2O$ | 1 | Total carbohydrate | <0.1 | 0.1 | <0.1 | 8.4 | 18 | 24 | 39 | 39 |
| | | Glucose | <0.1 | | <0.1 | <0.1 | <0.1 | 7 | 15 | 15 |
| HCl (1.0 M) saturated with LiCl | 1 | Total carbohydrate | 1.4 | 0.1 | 32 | 47 | 72 | 80 | 90 | 91 |
| | | Glucose | 0.2 | | <0.1 | 6.6 | 11 | 13 | 31 | 31 |
| HCl (1.0 M) saturated with LiCl | 1 | Total carbohydrate | 1.7 | 1.0 | 85 | 84 | 93 | 91 | 94 | 95 |
| | | Glucose | <0.1 | | 24 | 33 | 52 | 59 | 90 | 90 |
| HCl (1.0 M) saturated with LiCl | 3 | Total carbohydrate | 2.7 | 1.0 | 68 | 80 | 86 | 86 | 86 | 89 |
| | | Glucose | <0.1 | | 20 | 30 | 45 | 54 | 83 | 83 |
| $H_2O$ | 3 | Total carbohydrate | <0.1 | 1.0 | 7 | 9 | 18 | 29 | 50 | 50 |
| | | Glucose | <0.1 | | 10 | 14 | 16 | 27 | 49 | 49 |

EXAMPLE 8

Treatment of cellulose with solutions of Lithium chloride and lithium chloride/hydrochloric acid at elevated temperatures Two test solutions were prepared by placing portions (50 mg) of cellulose fibres in two test-tubes and adding thereto in one instance a saturated solution of lithium chloride (5.0 $cm^3$) and in the other a solution of hydrochloric acid (0.5M) saturated with lithium chloride. The tubes were sealed, kept in a refrigerator overnight, and then placed in a boiling water bath. After 5 minutes the tube containing HCl/LiCl was removed, as the cellulose had essentially dissolved, and cooled in an ice bath. The tube containing LiCl solution was kept in the boiling water bath for 12 hours. The solution and supernatant respectively were analysed for total carbohydrate employing standard solutions of D-glucose in saturated lithium chloride solution. The results are set out in Table 12. These results demonstrate that treatment with hydrochloric acid (0.5M) saturated with lithium chloride gives a high degree of solubilisation (ca 54%). The carbohydrate solubilised was shown by gel permeation chromatography to be largely glucose (5.0 mg $cm^{-3}$ out of 6.0 mg $cm^3$ solubilised) with the remainder mainly as a disaccharide.

TABLE 12

Solubilisation of cellulose fibres by LiCl (saturated) and HCl (0.5 M) saturated with LiCl.

| Solution | Concentration of total carbohydrate in supernatant |
|---|---|
| LiCl/HCl | 6.0 mg $cm^{-3}$ |
| LiCl | 2.4 mg $cm^{-3}$ |

EXAMPLE 9

Treatment of cellulose fibres with hydrochloric acid of various concentration saturated with Lithium chloride Samples (50 mg) of cellulose fibres were placed in test-tubes to each of which was added a solution (5.0 $cm^3$) of hydrochloric acid (0.1, 0.5, 1.0, 2.0, 3.0 or 4.0M) saturated with lithium chloride. The tubes were sealed and placed in a boiling water bath. Tubes were removed as soon as solubilisation was observed visually, or when significant discolouration was apparent. On removal the tubes were cooled in an ice bath and stored in a refrigerator until analysis for total carbohydrate in solution as in Example 8. The results obtained are set out in Table 13. The data in Table 13 demonstrates that hydrochloric acid (4.0M) saturated with lithium chloride had achieved essentially 100% solubilisation.

TABLE 13

Solubilisation of cellulose fibres by hydrochloric acid saturated with lithium chloride.

| HCl concentration in solution (M) | Time in heating bath | Total carbohydrate concentration in solution mg $cm^{-3}$ | % solubilised on basis of total carbohydrate analysis |
|---|---|---|---|
| 4.0 | 55 sec. | 11.2 | 105 |
| 3.0 | 55 sec. | 8.9 | 83 |
| 2.0 | 2 min 57 sec | 3.4 | 32 |
| 1.0 | 5 min. | 7.3 | 68 |
| 0.5 | 5 min. | 1.4 | 13 |
| 0.1 | 30 min. | no visible solubilisation | — |

EXAMPLE 10

Treatment of cellulose fibres with HCl (4.0M) containing various concentrations of lithium chloride The method of Example 9 as repeated using a fixed HCl concentration (4.0M) but varying lithium chloride concentrations. The lithium chloride concentrations used were 1.0, 2.0, 4.0, 8.0M and saturated. The results are set out in Table 14.

TABLE 14

Solubilisation of cellulose fibres by hydrochloric acid (4.0 M) containing various concentrations of lithium chloride.

| LiCl concentration in HCl (4.0 M) | Time in heating bath | Total carbohydrate concentration in solution mg $cm^3$ | solubilised on basis of total carbohydrate analysis |
|---|---|---|---|
| 1.0 M | 30 min. | 1.9 | 18 |
| 2.0 M | 30 min. | 4.2 | 39 |
| 4.0 M | 30 min. | 3.1 | 29 |
| 8.0 M | 9 min. | 8.0 | 76 |
| saturated | 45 sec. | 10.9 | 102 |

EXAMPLE 11

Treatment of cellulose fibres with hydrochloric acid of various concentrations saturated with lithium chloride with a pretreatment at room temperature prior to solubilisation at an elevated temperature The method of Example 9 was repeated save that the hydrochloric acid solutions of molarity 0.1, 0.5 and 1.0, saturated with lithium chloride, were employed and that the test solutions were allowed to stand for 60 hours at room temperature before heating. The results are set out in Table 15 and the data therein, when compared with Table 13, indicates that pretreatment increases cellulose solubilisation.

TABLE 15

Solubilisation of cellulose fibres on treatment with hydrochloric acid (0.1, 0.5 and 1.0 M) saturated with lithium chloride after pretreatment.

| HCl concentration in solution (M) | Time in heating bath | Total carbohydrate concentration in solution mg $cm^{-3}$ | % solubilised on basis of total carbohydrate analysis |
|---|---|---|---|
| 1.0 | 73 sec | 9.7 | 91 |
| 0.5 | 162 sec | 9.6 | 90 |
| 0.1 | 25 min | 10.2 | 95 |

EXAMPLE 12

Treatment of various cellulose containing materials with hydrochloric acid (1.0M) saturated with lithium chloride The materials examined were cellulose fibres, mechanical pulp, newsprint 1 (Daily Mirror), newsprint 2 (Observer, no ink) and a yeast glucan. Samples (50 mg) of each material were suspended in a solution (5 $cm^3$) of hydrochloric acid (1.0M) saturated with lithium chloride and treated as in Example 11. The solutions obtained were clarified by centrifugation prior to analysis for total carbohydrate and for molecular distribution by gel permeation chromatography. The results obtained are set out in Table 16. The data presented in Table 16 indicates that the cellulose fibres have been completely solubilised (within experimental error) and that the solubilised carbohydrate for the mechanical pulp and newsprint compares favourably with that available therein.

TABLE 16

Solubilisation of various cellulose containing materials with hydrochloric acid (1.0 M) saturated with lithium chloride.

| Material | Time of heating | Concentration of Total carbohydrate in solution mg $cm^{-3}$ | Relative molecular distribution (%) G1 | G2 | G3 |
|---|---|---|---|---|---|
| Cellulose fibres | 3.5 min | 10.2 | 94.2 | 5.0 | 0.8 |
| Mechanical pulp | 4.5 min | 6.5 | 92.9 | 5.3 | 1.8 |
| Newsprint 1 | 5.5 min | 7.1 | 96.7 | 3.3 | 0 |
| Newsprint 2 | 4.75 min | 6.1 | 92.0 | 2.4 | 5.6 |
| Yeast glucan | 3 min | 6.6 | — | — | — |

EXAMPLE 13

Treatment of various cellulose containing materials with hydrochloric acid (4.0M) saturated with lithium chloride The materials examined were cellulose fibres, mechanical pulp, newsprint 1 (Daily Mirror), newsprint 2 (Observer, no ink) and as controls glucose and cellobiose. Samples (50 mg) of each material were suspended in a solution (5.0 $cm^3$) of hydrochloric acid (4.0M) saturated with lithium chloride. The suspensions were sealed in glass tubes and placed in a boiling water bath. The tubes were then treated and analysed as in Example 8 for total carbohydrate and for molecular distribution by gel permeation chromatagraphy. The results obtained are set out in Table 17. The data indicates complete solubilisation of cellulose fibres.

TABLE 17

Solubilisation of cellulose containing materials by hydrochloric acid (4.0 M) saturated with lithium chloride.

| Material | Time of heating (minutes) | Total carbohydrate concentration in solution (mg $cm^{-3}$) |
|---|---|---|
| Cellulose | 1.33 | 10.5* |
| Mechanical pulp | 1.75 | 5.2 |
| Newsprint 1 | 1.75 | 5.7 |
| Newsprint 2 | 1.75 | 5.2 |
| Cellobiose | 1.0 | 11.0 |

TABLE 17-continued

Solubilisation of cellulose containing materials by hydrochloric acid (4.0 M) saturated with lithium chloride.

| Material | Time of heating (minutes) | Total carbohydrate concentration in solution (mg $cm^{-3}$) |
|---|---|---|
| Glucose | 1.0 | 9.8 |

*Relative molecular distribution (%): G1 (28.9), G2 (17.0), G3 (13.3), G4 (11.7), G5 (8.8), G6 (7.1), G7 (4.5), G8 (3.1), G9 (2.4), G10 (1.3), G11 (1.0), G12 (0.8).

EXAMPLE 14

Treatment of cellulose fibres with various acids in solutions saturated with inorganic salts Samples (50 mg) of cellulose were suspended in various solutions (5.0 $cm^3$) as specified in Table 18. The suspensions were either stored at 4° C. for 20 hours before placing in a boiling water bath or placed in a boiling water bath immediately, following the procedures described in Example 8. All tubes were kept in an ice bath after heating until ready for analysis for total carbohydrate. The results obtained are set out in Table 18(a) and Table 18(b).

TABLE 18(a)

Solubilisation of cellulose fibres with various acid/salt combinations

| Acid | Salt | Pretreatment at 4° C. | Heating time (min) | % solubilisation of cellulose |
|---|---|---|---|---|
| HCl(1.0 M) | LiCl(sat) | 20 hrs | 2.0 | 100 |
| +HBr(4.0 M) | LiBr(sat) | 0 | 1.33 | 100 |
| +HBr(1.0 M) | LiBr(sat) | 20 hrs | 2.5 | 100 |
| $H_2SO_4$(2.0 M) | $Li_2SO_4$(sat) | 0 | 30 | 3.5 |
| $H_2SO_4$(0.5 M) | $Li_2SO_4$(sat) | 20 hrs | 30 | 14.5 |
| HCl(4.0 M) | NaCl(sat) | 0 | 30 | 22 |
| HCl(4.0 M) | *$MgCl_2$(sat) | 0 | 30 | 30 |
| HCl(4.0 M) | *$MgCl_2$(sat) | 20 hrs | 30 | 49 |
| $H_2SO_4$(0.5 M) | LiCl(sat) | 20 hrs | 240 | 11 |
| TFA (1.0 M) | LiCl(sat) | 20 hrs | 240 | 31 ≠ |
| TCA(1.0 M) | LiCl(sat) | 20 hrs | 90 | 6 ≠ |
| $HNO_3$(1.0 M) | LiCl(sat) | 20 hrs | 240 | 0 |
| HCOOH(1.0 M) | LiCl(sat) | 20 hrs | 240 | 0 |
| $CH_3COOH$(1.0 M) | LiCl(sat) | 20 hrs | 90 | 0 |

+ Derived from a solution of HBr (45% w/v) in glacial acetic acid.
*Derived from $MgCl_26H_2O$.
≠ Forms two phases, upper phase analysed.

TABLE 18(b)

Solubilisation of cellulose fibres with a combination of hydrochloric acid saturated with lithium chloride and hydrochloric acid saturated with magnesium chloride.

| Solution | Pretreatment at 4° C. | Heating time (min) | % solubilisation of cellulose |
|---|---|---|---|
| HCl (4.0 M) saturated with LiCl, 1 part, and HCl (4.0 M) saturated with $MgCl_26H_2O$, 1 part. | none | 30 | 24 |

EXAMPLE 15

Treatment of cellulose fibres with hydrochloric acid (3.5M) alone

Samples (50 mg) of cellulose fibres were placed in test-tubes to each of which was added hydrochloric acid (3.5M, 5.0 $cm^3$). The tubes were sealed and placed in a boiling water bath. Tubes were removed after 2, 4, 8 and 12 hours. Solutions after 8 and 12 hours were yellow, and the residual cellulose blackened, whereas those at 2 and 4 hours were colourless and the residual cellulose white. Analysis of the supernatant solution was carried out for total carbohydrate. The results obtained are set out in Table 19. The data therein, when compared with Example 9 Table 13, demonstrates the effectiveness of the hydrochloric acid in combination with lithium chloride. Thus 17% solubilisation is achieved with HCl (3.5M) in 720 minutes as compared with complete solubisation in 55 seconds with HCl (4.0M) saturated with lithium chloride or 83% solubilisation in 55 seconds with HCl (3.0M) saturated with lithium chloride.

TABLE 19

Solubilisation of cellulose fibres by hydrochloric acid (3.5 M)

| Heating time (min) | % solubilised as expressed by total carbohydrate in solution |
|---|---|
| 120 | 2 |
| 240 | 5 |
| 480 | 14 |
| 720 | 17 |

EXAMPLE 16

Solubilisation and hydrolysis of cellulose fibres with various combinations of water, hydrochloric acid and lithium chloride at 50° C.

Samples of cellulose fibres were placed in screw cap bottles and the appropriate test solution (10 $cm^3$), as specified in Table 20, was added. The bottles were placed in a water bath at 50° and the contents stirred by means of a magnetic follower. Samples (0.1 $cm^3$) were removed at specifed time intervals, diluted with water (to 10 $cm^3$) and stored at 4° C. until analysis. Analyses for total carbohydrate and D-glucose were performed with appropriate dilution of samples at the higher cellulose concentrations. The results obtained are set out in Table 20. The data contained therein demonstrate the effectiveness of hydrochloric acid (4.0M) saturated with lithium chloride at solubilising cellulose fibres at 1, 5 or 10%; complete solubilisation being observed at 50° C. within one hour, within the limits of experimental error.

TABLE 20

Solubilisation of cellulose fibres under various treatments at 50° C.

| Cellulose concentration % w/v | Solution employed | Heating time (hours) | Total carbohydrate concentration in solution mg $cm^{-3}$ | D-glucose concentration in solution mg $cm^{-3}$ | Total carbohydrate solubilised (%) |
|---|---|---|---|---|---|
| 1.0 | HCl(4.0 M) | 0.5 | 9.0 | 3.3 | 97 |
| | saturated | 1.0 | 10.4 | 7.0 | |
| | with LiCl | 1.5 | 10.5 | 8.8 | |
| | | 2.0 | 10.5 | 10.2 | |
| | | 6.0 | 10.5 | 10.3 | |
| 1.0 | HCl(4.0 M) | 1.0 | 0.1 | 0.0 | 16 |
| | | 2.0 | 0.5 | 0.0 | |
| | | 3.0 | 1.0 | 0.0 | |
| | | 4.0 | 1.7 | 0.0 | |
| 1.0 | HCl(1.0 M) | 1.0 | 4.0 | 1.0 | 80 |
| | saturated | 2.0 | 7.6 | 3.4 | |
| | with LiCl | 3.0 | 8.4 | 5.3 | |
| | pretreated | 4.0 | 8.5 | 6.3 | |
| | at 4° C. for | 5.0 | 8.5 | 7.0 | |
| | 20 hours | 6.0 | 8.6 | 7.4 | |
| 5.0 | HCl(4.0 M) | 1.0 | 58.0 | 29.5 | 104 |
| | saturated | 2.0 | 55.5 | 34.5 | |
| | with LiCl | 3.0 | 55.5 | 45.1 | |
| | | 5.5 | 51.0 | 35.5 | |
| 10.0 | HCl(4.0 M) | 1.0 | 107.6 | 42.4 | 100 |
| | saturated | 2.0 | 106.0 | 61.9 | |
| | with LiCl | 3.0 | 104.7 | +65.3 | |
| | | 5.5 | 100.3 | 68.5 | |

+ Analysis of the relative molecular distribution of this sample indicated the following relative percentage composition: G1(57.1), G2(23.5), G3(7.7), G4(2.5), G5(1.2), G6(0.4), G7(0.2), G8(0.1), unidentified (7.4).

EXAMPLE 17

Solubilisation and hydrolysis of cellulose fibres by hydrochloric acid (4.0M) saturated with lithium chloride by treatment at 50° C. followed by an elevated temperature Samples (0.5 or 1.0 g) of cellulose fibres were placed in screw cap bottles to each of which was added hydrochloric acid (4.0M) saturated with lithium chloride (10.0 $cm^3$). These bottles were placed in a bath at 50° C. for either 1 or 2 hours, the contents being stirred with the aid of a magnetic follower. At the end of this first stage, aliquots (1.0 $cm^3$) were removed and placed in smaller bottles. These bottles were then immersed in a water bath at 80° C. or a boiling water bath. Bottles were removed at the specified time intervals, cooled and kept at 4° C. until analysed. The samples were diluted (0.1 $cm^3$ to 100 $cm^3$) prior to analysis for total carbohydrate, D-glucose and, where indicated, relative molecular distribution by gel permeation chromatography. The results obtained are set out in Tables 21 and 22. The solutions of hydrochloric acid (4.0M) saturated with lithium chloride were characterised by measurement of refractive index at 20° C. using the sodium D line. Solutions of various lithium chloride concentrations were also measured. These results are shown in Table 23. From this data, and the measured density, a solution of hydrochloric acid (4.0M) saturated with lithium chloride was estimated to contain:

HCl: 146.0 g $l^{-1}$
LiCl: 479.0 g $l^{-1}$
$H_2O$: 640.7 g $l^{-1}$

TABLE 21

Analysis of total carbohydrate and D-glucose during treatment of cellulose fibres with HCl (4.0 M) saturated with lithium chloride under various conditions.

| Cellulose Concentration (% w/v) | Time at 50° C. (hrs) | Subsequent temperature (°C.) | Time at subsequent temperature (min) | Total carbohydrate concentration (mg $cm^{-3}$) | D-glucose concentration (mg $cm^{-3}$) | Total carbohydrate in solution (%) |
|---|---|---|---|---|---|---|
| 10.0 | 1.0 | 100+ | 0 | 88 | 54 | 100 |
| | | | 1 | 98 | 58 | |
| | | | 2 | 96 | 73 | |
| | | | 3 | 107 | 80 | |
| | | | 4 | 94 | 70 | |
| | | | 5 | 98 | 66 | |
| | | | 10 | 71 | 55 | |
| 10.0 | 1.0 | 80 | 0 | 103 | 56 | 96 |
| | | | 2 | 99 | 51 | |
| | | | 4 | 98 | 62 | |
| | | | 6 | 100 | 68 | |
| | | | 8 | 99 | 73 | |
| | | | 10 | 101 | 65 | |
| | | | 12 | 91 | 64 | |
| | | | 14 | 96 | 63 | |
| 10.0 | 2.0 | 100+ | 0 | 79 | 56 | 80 |
| | | | 1 | 80 | 64 | |
| | | | 2 | 81 | 67 | |
| | | | 3 | 86 | 78 | |
| | | | 4 | 84 | 74 | |
| | | | 6 | 82 | 71 | |
| | | | 8 | 79 | 66 | |
| | | | 10 | 76 | 56 | |
| 5.0 | 1.0 | 100+ | 0 | 54 | 29 | 104 |
| | | | 1 | 55 | 38 | |
| | | | 2 | 56 | 45 | |
| | | | 3 | 56 | 41 | |
| | | | 4 | 54 | 40 | |
| | | | 5 | 53 | 38 | |
| | | | 6 | 50 | 36 | |
| | | | 7 | 48 | 34 | |
| | | | 8 | 47 | 27 | |
| 5.0 | 1.0 | 90 | 0 | 53 | 28 | 101 |
| | | | 1 | 53 | 32 | |
| | | | 2 | 53 | 35 | |
| | | | 3 | 54 | 38 | |
| | | | 5 | 52 | 44 | |
| | | | 6 | 52 | 43 | |
| | | | 7 | 49 | 42 | |
| | | | 8 | 49 | 42 | |

+immersion in a boiling water bath, 100° C. nominal.

TABLE 22

Relative molecular distribution of carbohydrate solubilised by HCl (4.0 M) saturated with lithium chloride.

| Cellulose concentration (% w/v) | Temperature conditions+ | Relative molecular distribution (%) G1 | G2 | G3 | G4 | G5 | Unidentified |
|---|---|---|---|---|---|---|---|
| 10.0 | 50° C. 60 min<br>100° C. 3 min | 65.9 | 19.8 | 3.9 | 0.8 | 0.2 | 9.4 |
| 10.0 | 50° C. 60 min<br>100° C. 7 min | 60.3 | 21.6 | 4.4 | 0.9 | 0.2 | 12.6 |
| 10.0 | 50° C. 120 min<br>100° C. 3 min | 65.3 | 23.0 | 4.3 | 0.8 | 0.8 | 6.3 |
| 5.0 | 50° C. 60 min<br>100° C. 2 min | 81.8 | 10.6 | 1.3 | 0.2 | — | 6.1 |

+100° C. nominal, immersion in a boiling water bath.

TABLE 23

Refractive index data for lithium chloride solutions

| Solution | $n_D^{20}$ |
|---|---|
| HCl (4.0 M), LiCl (9.0 M) | 1.4180 |
| HCl (4.0 M), LiCl (10.0 M) | 1.4251 |
| HCl (4.0 M), LiCl (11.0 M) | 1.4300 |
| HCl (4.0 M), LiCl (sat) | 1.4319 |
| LiCl (12 M) | 1.4202 |
| LiCl (13 M) | 1.4262 |
| LiCl (14 M) | 1.4322 |

TABLE 23-continued

Refractive index data for lithium chloride solutions

| Solution | $n_D^{20}$ |
|---|---|
| LiCl (sat) | 1.4343 |

EXAMPLE 18

Solubilisation and hydrolysis of starch (Amylum maydis) by hydrochloric acid (2.0M) saturated with magnesium chloride 6.$H_2O$ by treatment at 50° or at 50° and 90°

Samples (2.0 g) of starch (Amylum maydis) were placed in screw capped containers to each of which was added a solution (20.0 $cm^3$) of hydrochloric acid (2.0M) saturated with magnesium chloride $6H_2O$. The containers were immersed in a constant temperature bath at 50° for 30 to 180 minutes the contents being stirred by means of a magnetic follower. After appropriate time intervals certain containers were transferred to a bath at 90° for up to twenty minutes. After cooling the total carbohydrate and D-glucose contents of the solutions were determined. The results are set out in Table 24. Control solutions of hydrochloric acid (1.0M and 4.0M) were also employed as a solubilisation and hydrolysis medium. It can be seen that under these conditions hydrolysis to glucose is negligable in the absence of the magnesium chloride and that the ready solubilisation achieved in the presence of magnesium chloride is obtained at higher levels of hydrochloric acid.

TABLE 24

Solubilisation and hydrolysis of starch by hydrochloric acid and hydrochloric acid saturated with magnesium chloride

| Time at 50° (min) | Time at 90° (min) | D-glucose % | Time at 50° (min) | Time at 90° (min) | D-glucose % |
|---|---|---|---|---|---|
| 20 | — | 5.6 | 60 | 0 | 37.8 |
| 40 | — | 21.9 | 60 | 2 | 38.1 |
| 60 | — | 38.8 | 60 | 4 | 39.9 |
| 90 | — | 56.5 | 60 | 6 | 51.7 |
| 120 | — | 69.0 | 60 | 8 | 65.1 |
| 150 | — | 73.6 | 60 | 10 | 73.3 |
| 180 | — | 75.8 | 60 | 12 | 76.1 |
| | | | 60 | 14 | 82.6 |
| 30 | 0 | 13.4 | 180 | 0 | 65.1 |
| 30 | 2 | 14.2 | 180 | 2 | 67.2 |
| 30 | 4 | 50.2 | 180 | 4 | 73.1 |
| 30 | 6 | 70.5 | 180 | 6 | 73.6 |
| 30 | 8 | 75.6 | 180 | 8 | 77.4 |
| 30 | 10 | 79.6 | 180 | 10 | 80.1 |
| 30 | 12 | 78.6 | 180 | 12 | 87.3 |
| 30 | 14 | 79.9 | 180 | 14 | 82.3 |

| Time at 50° (min) | Solubilisation (%) | D-glucose (%) | HCl concentration (M) |
|---|---|---|---|
| 10 | 24.6 | 0.01 | 4.0 |
| 20 | 51.3 | | |
| 40 | 72.6 | | |
| 60 | 81.9 | | |
| 10 | 9.4 | 0.01 | 1.0 |
| 20 | 12.5 | | |
| 40 | 17.2 | | |
| 60 | 24.6 | | |

EXAMPLE 19

Solubilisation and hydrolysis of starch by hydrochloric acid (2.0M) saturated with magnesium chloride $6H_2O$ with and without the addition of water during the hydrolysis phase The procedure of Example 18 was followed using starch (1.5 g) in hydrochloric acid (2.0M) saturated with magnesium chloride $6H_2O$ (10 $cm^3$). After three hours at 50° water (0.15 $cm^3$) was added to one set of solutions and hydrolysis continued at 50°. The D-glucose content of the solutions after various times are set out in Table 25.

TABLE 25

Solubilisation and hydrolysis of starch by hydrochloric acid containing magnesium chloride with and without water addition during the hydrolysis phase

| No water addition | | Water added after 3.0 hours | |
|---|---|---|---|
| Time at 50° (min) | D-Glucose (%) | Time at 50° (min) | D-glucose (%) |
| 30 | 16.7 | 30 | 19.4 |
| 60 | 47.2 | 60 | 50.3 |
| 120 | 76.5 | 120 | 79.3 |
| 180 | 80.3 | 180 | 85.5 |
| 210 | 80.2 | 210 | 88.1 |
| 240 | 81.7 | 240 | 92.4 |

We claim:

1. A process for the treatment of a glycosidically linked carbohydrate having reducing groups to produce solubilisation and hydrolysis of at least one glycosidic linkage in the carbohydrate to produce a sugar selected from the group consisting of soluble oligosaccharides and glucose, comprising contacting a glycosidically linked carbohydrate having reducing groups at a temperature within the range 50° C. to 100° C. and for a time period within the range 45 seconds to 6 hours with a mixture comprising an aqueous inorganic acid at a concentration within the range 1 to 10 molar and a compound of a metal selected from the group consisting of lithium halides, magnesium halides and calcium halides and precursors of said halides which precursors are selected from the group consisting of carbonates, bicarbonates and hydroxides, the halide being present at a concentration within the range 1 molar to saturation concentration in the acid.

2. A process according to claim 1 wherein the glycosidically linked carbohydrate having reducing groups is cellulose and is treated to produce a product selected from the group consisting of cellodextrin, cellotriose, cellobiose and glucose and wherein the halide is a halide of lithium.

3. A process according to claim 1 wherein the glycosidically linked carbohydrate having reducing groups is starch and is treated to produce D-glucose or a mixture of sugars containing D-glucose and wherein the halide is a halide of a metal selected from the group consisting of magnesium and calcium.

4. A process according to claim 3 wherein the halide is a halide of magnesium.

5. A process according to claim 1 wherein the halide is a chloride.

6. A process according to claim 1 wherein the inorganic acid is hydrochloric acid.

7. A process according to claim 1 wherein a quantity of water sufficient to replace that which is consumed is added during the process.

8. A process for treatment of a glycosidically linked carbohydrate having reducing groups to produce solubilisation and hydrolysis of at least one glycosidic linkage in the carbohydrate to produce a sugar selected from the group consisting of soluble oligosaccharides and glucose, comprising contacting a glycosidically linked carbohydrate having reducing groups at a temperature within the range 50° C. to 100° C. and for a time period within the range 45 seconds to 6 hours with a mixture comprising an aqueous inorganic acid at a concentration within the range 1 to 10 molar and a compound of a metal selected from the group consisting of lithium halides, magnesium halides and calcium halides and precursors of said halides which precursors are selected from the group consisting of carbonates, bicarbonates and hydroxides, the halide being present at a concentration effective to achieve solubilization and hydrolysis of at least one glycosidic linkage in the carbohydrate.

* * * * *